United States Patent [19]

Thurman et al.

[11] Patent Number: 5,227,544
[45] Date of Patent: Jul. 13, 1993

[54] PROCESS FOR THE PRODUCTION OF 2-ETHYLHEXANOL

[75] Inventors: Laurance R. Thurman, Clute; James B. Harris, Pearland, both of Tex.

[73] Assignee: BASF Corporation, Parsippany, N.J.

[21] Appl. No.: 917,526

[22] Filed: Jul. 17, 1992

Related U.S. Application Data

[63] Continuation of Ser. No. 656,544, Feb. 15, 1991, abandoned.

[51] Int. Cl.$^5$ ............... C07C 29/141; C07C 31/125; C07C 45/85; C07C 45/78
[52] U.S. Cl. .................................. 568/881; 568/491; 568/492
[58] Field of Search .................. 568/491, 492, 881

[56] References Cited

U.S. PATENT DOCUMENTS

| | | | |
|---|---|---|---|
| 1,556,067 | 10/1925 | Bogin | 568/492 |
| 1,724,761 | 8/1929 | Holden | 568/492 |
| 3,288,866 | 11/1966 | Cooper | 568/881 |
| 3,491,158 | 1/1970 | Reich | 568/881 |
| 4,138,588 | 2/1979 | Tummes et al. | 568/881 |
| 4,426,541 | 1/1984 | King | 568/881 |
| 4,684,750 | 8/1987 | Kessen et al. | 568/883 |
| 4,960,960 | 10/1990 | Harrison et al. | 568/881 |

FOREIGN PATENT DOCUMENTS

| | | | |
|---|---|---|---|
| 1202326 | 3/1986 | Canada | 568/492 |
| 988804 | 1/1983 | U.S.S.R. | 568/492 |

*Primary Examiner*—Joseph E. Evans

[57] ABSTRACT

The present invention provides a process for producing 2-ethylhexanol having a reduced concentration of 2-ethyl-4-methyl pentanol. It may be practiced in its most basic form as a distillation. It may also be practiced as part of a multi-stage continuous process. In either form it begins with a feed stream comprising n-butyraldehyde containing as a contaminant, isobutyraldehyde, complexes of isobutyraldehyde, oligomers of isobutyraldehyde and mixtures thereof, to which is added or introduced, an amount of water effective to hydrolyze the oligomeric contaminants to the monomeric form of isobutyraldehyde during distillation. The water containing aldehyde mixture is introduced to a distillation zone with a residence time and at a temperature sufficient to hydrolyze the oligomeric contaminants to and then distill substantially all of the isobutyraldehyde overhead. In the multi-stage process, the distilled n-butyraldehyde is then subjected to an alkali-catalyzed aldol condensation reaction to produce 2-ethylhex-2-enal. In a third stage, the 2-ethylhex-2-enal is hydrogenated with a catalyst under temperature and pressure conditions conducive to hydrogenation to produce 2-ethylhexanol.

6 Claims, No Drawings

PROCESS FOR THE PRODUCTION OF 2-ETHYLHEXANOL

This is a continuation of co-pending application Ser. No. 07/656,544 filed on Feb. 15, 1991, now abandoned.

FIELD OF THE INVENTION

The present invention relates to the preparation of 2-ethylhexanol. More particularly, it relates to a process for reducing the 2-ethyl-4-methyl pentanol content in 2-ethylhexanol.

BACKGROUND OF THE INVENTION

2-Ethylhexanol is used in large quantities as an esterification component, e.g. for the preparation of dioctyl phthalate as a plasticizer for PVC. 2-Ethylhexanol is made by alkali-catalyzed condensation of n-butyraldehyde to yield the unsaturated aldehyde, 2-ethyl-hex-2-enal, which is then hydrogenated to yield the desired 2-ethylhexanol.

Various processes for the production of n-butyraldehyde are known. It is also known that n-butyraldehyde will contain, as an impurity, isobutyraldehyde and that oligomers of isobutyraldehyde will be present due to hydroformylation. These impurities will, if not removed, lead to the formation of 2-ethyl-4-methyl-pentenal during the preparation of 2-ethyl-hex-2-enal. The 2-ethyl-4-methyl-pentenal is then hydrogenated to the alcohol, 2-ethyl-4-methyl pentanol during the preparation of 2-ethylhexanol and cannot be economically removed.

2-Ethyl-hex-2-enal is prepared by the alkali-catalyzed aldol condensation of n-butyraldehyde.

2-Ethylhexanol is prepared by the hydrogenation of 2-ethylhex-2-enal (oxo successive product). In this process hydrogenation can occur both in the gaseous phase (DE-AS 11 52 393) and in the liquid phase (DE-AS 19 49 296). In these processes higher catalyst loads can generally be achieved in the liquid phase due to improved dissipation of heat.

2-Ethylhexanol is used for production of the plasticizer, di-2-ethylhexyl phthalate and for many other uses. The presence of even minor amounts of contaminants will reduce purity and may affect the end use and even render it unacceptable. Accordingly, there exists a need in the art to reduce the quantity of contaminants in general and 2-ethyl-4-methyl pentanol in particular.

SUMMARY OF THE INVENTION

The present invention provides a process for producing 2-ethylhexanol having a reduced concentration of 2-ethyl-4-methyl pentanol. It may be practiced in its most basic form as a distillation. It may also be practiced as part of a multi-stage continuous process. In either form it begins with a feed stream comprising n-butyraldehyde containing as a contaminant, isobutyraldehyde, complexes of isobutyraldehyde, oligomers of isobutyraldehyde and mixtures thereof, to which is added or introduced, an amount of water effective to hydrolyze the oligomeric contaminants to the monomeric form of isobutyraldehyde during distillation. The water containing aldehyde mixture is introduced to a distillation zone with a residence time and at a temperature sufficient to hydrolyze the oligomeric contaminants to and then distill substantially all of the isobutyraldehyde overhead. In the multi-stage process, the distilled n-butyraldehyde is then subjected to an alkali-catalyzed aldol condensation reaction to produce 2-ethylhex-2-enal. In a third stage, the 2-ethylhex-2-enal is hydrogenated with a catalyst under temperature and pressure conditions conducive to hydrogenation to produce 2-ethylhexanol.

DETAILED DESCRIPTION OF THE PREFERRED EMBODIMENTS

The present invention may be practiced in a single stage or in multiple stages. A first, essential stage comprises the distillation of n-butyraldehyde. In a second stage, the distilled n-butyraldehyde from the first stage is subjected to an aldol condensation or enalization reaction to produce 2-ethylhex-2-enal. In the third stage is, the 2-ethylhex-2-enal is hydrogenated to produce 2-ethylhexanol. A fourth stage may be employed to distill the 2-ethylhexanol.

In the first stage, which may be referred to as a distillation zone and which typically employs one or more conventional distillation columns or towers, n-butyraldehyde containing isobutyraldehyde, complexes of isobutyraldehyde, oligomers of isobutyraldehyde and mixtures thereof is distilled. Typically, this distillation will be carried out in a single distillation tower where the distillation operates at a temperature and for a residence time sufficient to distill isobutyraldehyde overhead; preferably at a head temperature in the range of from about 70° to about 90° C., which as one skilled in the art will appreciate, will be selected and will vary depending on column pressure.

The actual temperatures and number of distillation columns employed may vary depending on the crude n-butyraldehyde composition and the specific equipment used in the process.

It is known that isobutyraldehyde will complex or trimerize resulting in a product or oligomer which is difficult to remove during distillation of n-butyraldehyde. It is also known that these oligomers will, when subjected to heat, hydrolyze to the monomeric form during the enalization stage. In this stage the monomeric form is converted to 2-ethyl-4-methyl-pentenal which in the third or hydrogenation stage is converted to 2-ethyl-4-methyl-pentanol.

Accordingly, it has been discovered that if water is added to the n-butyraldehyde feed to the distillation column in an amount effective to hydrolyze the isobutyraldehyde oligomers to the monomeric form during distillation, they can be stripped from the n-butyraldehyde, thereby reducing the amount of isobutyraldehyde which reacts to form 2-ethyl-4-methyl-pentenal during aldol condensation and subsequent hydrogenation of the 2-ethyl-4-methyl-pentenal to 2-ethyl-4-methyl pentanol during the hydrogenation stage. By this method the content of 2-ethyl-4-methyl-pentanol in the final product can be substantially reduced; typically from a range of from about 0.2 to about 0.4 wt. % without the water addition to less than 0.2 wt. %, preferably to within a range of from about 0.08 to about 0.1 wt. % with the water addition, based on 2-ethylhexanol. The degree of improvement will vary with the amount of water added, with increasing amounts of water tending to give increasing reductions in the amount of 2-ethyl-4-methyl-pentanol in the 2-ethylhexanol.

Preferably, water is added in the range of from about 0.05 to about 2 wt. %, more preferably from about 0.5 to about 1.5 wt. %, and even more preferably from about 0.7 to about 1 wt. %, based on the crude n-/isobutyraldehyde mixture. The water will typically be added as a component of the aldehyde feed but it may also be added to the tower reflux or to the upper portion or lower portion of the distillation tower or towers as may be determined by one skilled in the art.

In the absence of water addition, the isobutyraldehyde and oligomers of isobutyraldehyde present in the crude n-/iso-butyraldehyde mixture both contribute to the ultimate formation of 2-ethyl-4-methyl pentanol, with the oligomers having a potentially greater contribution because they, unlike the monomeric isobutyraldehyde, are not readily removed during distillation. When the process of the present invention is employed, the oligomers are converted to isobutyraldehyde which is substantially removed through distillation. While some isobutyraldehyde and some oligomer remain after distillation and are ultimately converted to 2-ethyl-4-methyl pentanol, the contribution to the formation of 2-ethyl-4-methyl pentanol represented by the oligomers substantially reduced which, in turn, results in an overall reduction in the amount of 2-ethyl-4-methyl pentanol in the 2-ethylhexanol.

In the second stage, any conventional enalization reaction typically used to produce 2-ethylhex-2-enal from n-butyraldehyde may be employed. The enalization reaction is typically conducted in a counter-current (or co-current) reactor in the presence of an alkali catalyst which is preferably selected from the group consisting of alkali metal hydroxides, more preferably sodium hydroxide, in an amount sufficient to catalyze the aldol condensation of n-butyraldehyde to 2-ethylhex-2-enal. This is a conventional reaction well known to those skilled in the art.

In the third stage, any of the conventional hydrogenation processes for the production of 2-ethylhexanol such as the medium pressure process, or the processes disclosed in U.S. Pat. Nos. 4,960,960 or 4,626,604 may be employed. This reaction is a conventional one well known to those skilled in the art.

The process is not specific to any particular hydrogenation reaction or to any particular catalyst composition. Although cobalt catalysts may be used, more recently the use of rhodium complex catalysts has been preferred since these offer the advantages of lower operating pressure, ease of product recovery, and high n-/iso-aldehyde molar ratios. Typical operating conditions for such rhodium complex hydroformylation catalysts can be found in U.S. Pat. Nos. 3,527,809, 4,148,830, EP-A-Nos. 0096986, 0096987, and 0096988. For example, 2-ethylhex-2-enal can be made by condensation of 2 moles of n-butyraldehyde. The aldehyde hydrogenation reaction then produces 2-ethylhexanol from 2-ethylhex-2-enal. However, in such aldehyde hydrogenation reactions there can be used any of the conventionally used metal catalysts.

Typically, the hydrogenation will employ first and second hydrogenation zones. The first hydrogenation zone may comprise an adiabatic reactor, a reactor with an internal cooling coil, or a shell and tube reactor. In the case of a shell and tube reactor the catalyst may be packed in the tubes with coolant passing through the shell or it may be the shell that is packed with catalyst with coolant flow through the tubes. The first hydrogenation zone is generally operated as a trickle bed reactor. In this case the hydrogen containing gas of step (b) is generally admixed with the liquid phase upstream from the first hydrogenation zone and is partly dissolved therein. At the upper end of the first hydrogenation zone the concentration of unsaturated organic compound is at its highest in the liquid phase; hence the rate of hydrogenation is greatest at the upper end of the first hydrogenation zone.

As the liquid phase passes downwardly through the first hydrogenation zone co-currently with the hydrogen it becomes depleted in respect of hydrogenatable material and to some extent in respect of dissolved hydrogen and the partial pressure of any inert gas or gases present rises and the partial pressure of hydrogen falls as the hydrogen is consumed by the chemical reactions taking place in the first hydrogenation zone. Hence at the lower end of the first hydrogenation zone the driving force for the hydrogenation reaction is relatively low. The intermediate reaction product exiting the lower end of the first hydrogenation zone accordingly usually still contains a minor amount of chemically unsaturated hydrogenatable material.

Generally speaking the hydrogenation conditions in the first hydrogenation zone are selected so as to effect hydrogenation of from about 75% to about 99% or more of the hydrogenatable unsaturated groups present in the unsaturated organic material supplied to the first hydrogenation zone. Typically the hydrogenation is completed to an extent of from about 85% to about 99.5% in the first hydrogenation zone. In some cases, however, the extent of hydrogenation may be higher than this, e.g. about 99.8% or even up to about 99.99%, in the first hydrogenation zone.

In the second hydrogenation zone the intermediate reaction product from the first hydrogenation zone is fed in liquid form in co-current with a downward flow of the hydrogen-containing feed gas. The second hydrogenation zone can be operated on a once-through basis; alternatively the intermediate reaction can be admixed with recycled product, recovered from the lower end of the second hydrogenation zone so that the second hydrogenation zone is operated on a partial recycle basis. This may be desirable from the standpoint of fluid bed dynamics so as to ensure that the or each bed of catalyst is adequately wetted.

The following examples are provided in order to further illustrate the invention without limiting its scope.

EXAMPLES

Comparative Example

2-Ethylhexanol was produced using the multi-stage process described above in the specification. Water was not added during the aldehyde distillation. The 2-ethyl-4-methyl-pentanol content in the 2-ethylhexanol product was about 0.35 wt. %. The system was operated at the preferred conditions described in the specification.

Example 1

2-Ethylhexanol was produced as set forth in the Comparative Example with the exception that water was added to the feed of the aldehyde distillation tower in an amount equalling 0.9 wt. %. The 2-ethyl-4-methyl-pentanol content in the 2-ethylhexanol product to about 0.10 wt. %.

Example 2

2-Ethylhexanol was produced as set forth in the Comparative Example with the exception that water was added to the feed of the aldehyde distillation tower in an amount equalling 0.45 wt. %. The 2-ethyl4-methyl-pentanol content in the 2-ethylhexanol product was reduced to about 0.2 wt. %.

We claim:

1. A process for producing n-butyraldehyde having reduced contaminants for use in producing 2-ethylhexanol having a reduced concentration of 2-ethyl-4-methyl pentanol, comprising introducing a crude n-/iso-butyraldehyde mixture comprising n-butyraldehyde and as a contaminant, isobutyraldehyde, complexes of isobutyraldehyde, oligomers of isobutyraldehyde and mixtures thereof in a distillation column, and introducing from about 0.05 to about 2 wt. %, based on the crude n-/iso-butyraldehyde mixture, of water effective to hydrolyze the oligomeric contaminants to the monomeric form of isobutyraldehyde during distillation, and then distilling this mixture in a distillation zone at a temperature and for a residence time sufficient to hydrolyze the oligomeric contaminants to and then distill substantially all of the isobutyraldehyde overhead.

2. A process according to claim 1, in which the water is present in an amount of from about 0.5 to about 1.5 wt. %.

3. A process according to claim 1, in which the n-butyraldehyde mixture is distilled at a head temperature in the range of from about 70° to about 90° C.

4. A multi-stage continuous process for producing 2-ethylhexanol having a reduced concentration of 2-ethyl-4-methyl pentanol, comprising:

(a) in a first stage, introducing a crude n-/iso-butyraldehyde mixture comprising n-butyraldehyde and as a contaminant, isobutyraldehyde, complexes of isobutyraldehyde, oligomers of isobutyraldehyde and mixtures thereof in a distillation column, and introducing from about 0.05 to about 2 wt. %, based on the crude n-/iso-butyraldehyde mixture, of water effective to hydrolyze the oligomeric contaminants to the monomeric form of isobutyraldehyde during distillation thereby reducing the amount of isobutyraldehyde which reacts to form 2-ethyl-4-pentenal during the second stage and subsequent hydrogenation of the 2-ethyl-4-ethyl-4-methyl pentanol during the third stage, and then distilling this mixture in a distillation zone at a temperature and for a residence time sufficient to hydrolyze the oligomeric contaminants to and then distill substantially all of the isobutyraldehyde overhead.

5. A process according to claim 4, including a fourth stage in which the 2-ethylhexanol is distilled.

6. A process according to claim 4, in which the water in the first stage is added in an amount of from about 0.5 to about 1.5 wt. %.

* * * * *